United States Patent [19]

Sawamura et al.

[11] Patent Number: 6,051,061
[45] Date of Patent: Apr. 18, 2000

[54] CALCIUM PHOSPHATE CEMENTS AND CALCIUM PHOSPHATE CEMENT COMPOSITIONS

[75] Inventors: Takenori Sawamura; Masateru Hattori; Masahiko Okuyama, all of Nagoya, Japan

[73] Assignee: NGK Spark Plug Co., Ltd., Aichi, Japan

[21] Appl. No.: 09/273,731

[22] Filed: Mar. 22, 1999

[30] Foreign Application Priority Data

| Mar. 23, 1998 | [JP] | Japan | 10-095294 |
| Mar. 23, 1998 | [JP] | Japan | 10-095295 |
| Jan. 27, 1999 | [JP] | Japan | 11-018822 |

[51] Int. Cl.$^7$ ................................................ C04B 12/02
[52] U.S. Cl. ............................ 106/691; 106/35; 106/690
[58] Field of Search ........................... 106/690, 35, 691

[56] References Cited

U.S. PATENT DOCUMENTS

| Re. 33,161 | 2/1990 | Brown et al. ........................ 423/308 |
| 4,673,508 | 6/1987 | Coleman et al. ..................... 210/698 |
| 5,180,426 | 1/1993 | Sumita .................................... 106/35 |
| 5,281,404 | 1/1994 | Sumita .................................. 423/305 |

FOREIGN PATENT DOCUMENTS

| 0 298 501 A2 | 1/1989 | European Pat. Off. ......... A61K 6/06 |
| 0 323 632 A1 | 7/1989 | European Pat. Off. ......... A61K 6/06 |
| 0 298 501 B1 | 4/1992 | European Pat. Off. ......... A61K 6/06 |
| 0 323 632 B1 | 7/1992 | European Pat. Off. ......... A61K 6/06 |
| 0 436 499 B1 | 10/1996 | European Pat. Off. ......... C01B 25/32 |
| 54-130449 | 10/1979 | Japan . |
| 59-88351 | 5/1984 | Japan ............................. C04B 13/00 |
| 59-222408 | 12/1984 | Japan . |
| 62-083348 | 4/1987 | Japan ............................. C04B 28/34 |
| 63-166532 | 7/1988 | Japan . |
| 1-100048 | 4/1989 | Japan ............................. C04B 28/34 |
| 2-77261 | 3/1990 | Japan ............................. A61L 25/00 |
| 2-102165 | 4/1990 | Japan ............................. C04B 35/00 |
| 3-112843 | 5/1991 | Japan ............................. C04B 28/34 |
| 3-141955 | 6/1991 | Japan ............................. A61L 27/00 |
| 6-199622 | 7/1994 | Japan . |
| 7-289627 | 11/1995 | Japan ............................. A61L 27/00 |
| 2 074 702 | 3/1997 | Russian Federation . |
| 2 248 232 | 4/1992 | United Kingdom ............ C04B 12/02 |
| 96/02259 | 2/1996 | WIPO .......................... A61K 31/725 |

OTHER PUBLICATIONS

Chemical Abstract No. 111:28493, Sugawara et al, "Formation of hydroxyapatite . . . phosphate mixtures", J. Nihon Univ. Sch. Dent. (1989), 31(1), 372–81.

Kazumi Kodama et al., "The Development of a High–Performance AE Water Reducing Agent for Enhancing Strength of Cement", Cement and Concrete, No. 546, pp. 24–32 (Aug. 1992).

Japanese Society of Orthopaedic Ceramic Implants, 1990, "Orthopaedic Ceramic Implants", vol. 10, pp. 43–47 (no month).

European Search Report (Nov. 1998).

*Primary Examiner*—Anthony Green
*Attorney, Agent, or Firm*—Sughrue, Mion, Zinn, Macpeak & Seas, PLLC

[57] ABSTRACT

A calcium phosphate cement or the like which shows a low viscosity and excellent handleability in the step of kneading and achieves a high strength of the hardened body even though a kneading liquid is used in a small amount. A calcium phosphate cement containing a polysaccharide powder and 0.05 to 5% by weight of an N-alkyl-D-glucamine such as N-methyl-D-glucamine; or a calcium phosphate cement containing a calcium phosphate powder and a specific alkanolamine such as monoethanolamine. A calcium phosphate cement composition containing a calcium phosphate powder and a kneading liquid comprising an aqueous solution containing 0.1 to 10% by weight of an N-alkyl-D-glucamine such as N-methyl-D-glucamine or a kneading liquid containing a definite amount of a specific alkanolamine such as monoethanolamine.

13 Claims, 2 Drawing Sheets

CALCIUM PHOSPHATE CEMENTS AND CALCIUM PHOSPHATE CEMENT COMPOSITIONS

FIELD OF THE INVENTION

This invention relates to calcium phosphate cements and calcium phosphate cement compositions for medical or dental uses. More particularly, it relates to cements containing specific amine compounds and cement compositions having kneading liquids comprising aqueous solutions of specific amine compounds. The cements and cement compositions according to the present invention are usable as biological cements and cement compositions for forming artificial bones, artificial joints, artificial tooth roots, etc.

BACKGROUND OF THE INVENTION

A large number of medical cements of various compositions have previously been proposed for use in living bodies. Among all, calcium phosphate cements for living bodies have an advantage in that, this kind of cement upon hardening changes into a bioactive hydroxyapatite, and hence results in a hardened cement having excellent bioaffinity.

Many of these calcium phosphate cements for living bodies comprise tetracalcium phosphate as the main component. For example, U.S. Pat. No. 4,612,053 discloses cements comprising tetracalcium phosphate and calcium hydrogen phosphate as the main components. It is also known that the hardening properties of these calcium phosphate cements widely vary depending on the amount of liquid employed in the step of kneading. That is, the hardening time is shortened while the strength of the hardened body is elevated with a decrease in the kneading liquid employed (1990, Orthopaedic Ceramic Implant Vol. 10, p. 43–47).

When a kneading liquid is used in a small amount, however, the kneaded body becomes highly viscous and thus the handleability is deteriorated in the step of kneading. When such a cement is filled into a defective site of a bone, etc., cracks or voids are frequently formed therein and thus the strength of the hardened body is deteriorated. To obtain a kneaded body having sufficient handleability, it is therefore necessary to minimize the amount of the kneading liquid. In the field of cements for industrial use, on the other hand, it is known to use water reducing agents, AE water reducing agents, etc. to decrease the amount of kneading liquids while preventing the deterioration in the handleability. However, it is undesirable to apply these water reducing agents to cements to be used in living bodies, since no attention is paid to the safety in vivo with respect to these water reducing agents.

When such a calcium phosphate cement is kneaded and then immediately brought into contact with a pseudo body fluid, water penetrates into the kneaded body and disintegrates the same. Thus, there arise some troubles that the cement paste fails to retain its shape and inflammatory reactions are caused. Consequently, two different methods have been used to apply the cement to a body part where body fluids are present in a large amount. The first method is to apply a cement paste, not immediately after kneading, but instead after it has hardened to some degree. The second method is to apply the cement paste after removal of the body fluids from the body part and after homeostasis, etc. However, the cement paste which has hardened to some degree is difficult to handle and has poor handleability in, for example, filling up a defective part.

SUMMARY OF THE INVENTION

To solve the above-mentioned problems, the present invention aims at providing a calcium phosphate cement and a calcium phosphate cement composition capable of showing a regulated viscosity in the step of kneading and giving a kneaded body with excellent handleability, even though a kneading liquid is used at a low proportion to the calcium phosphate cement or the calcium phosphate cement composition. The present invention further aims at providing a cement and a cement composition being excellent in shape-impartation, capable of giving a kneaded body which retains its shape without disintegration when it is applied to a body part and thus brought into contact with body fluids immediately after kneading, and capable of giving a hardened body with a high strength within a short hardening time.

DETAILED DESCRIPTION OF THE INVENTION

Figure 1:
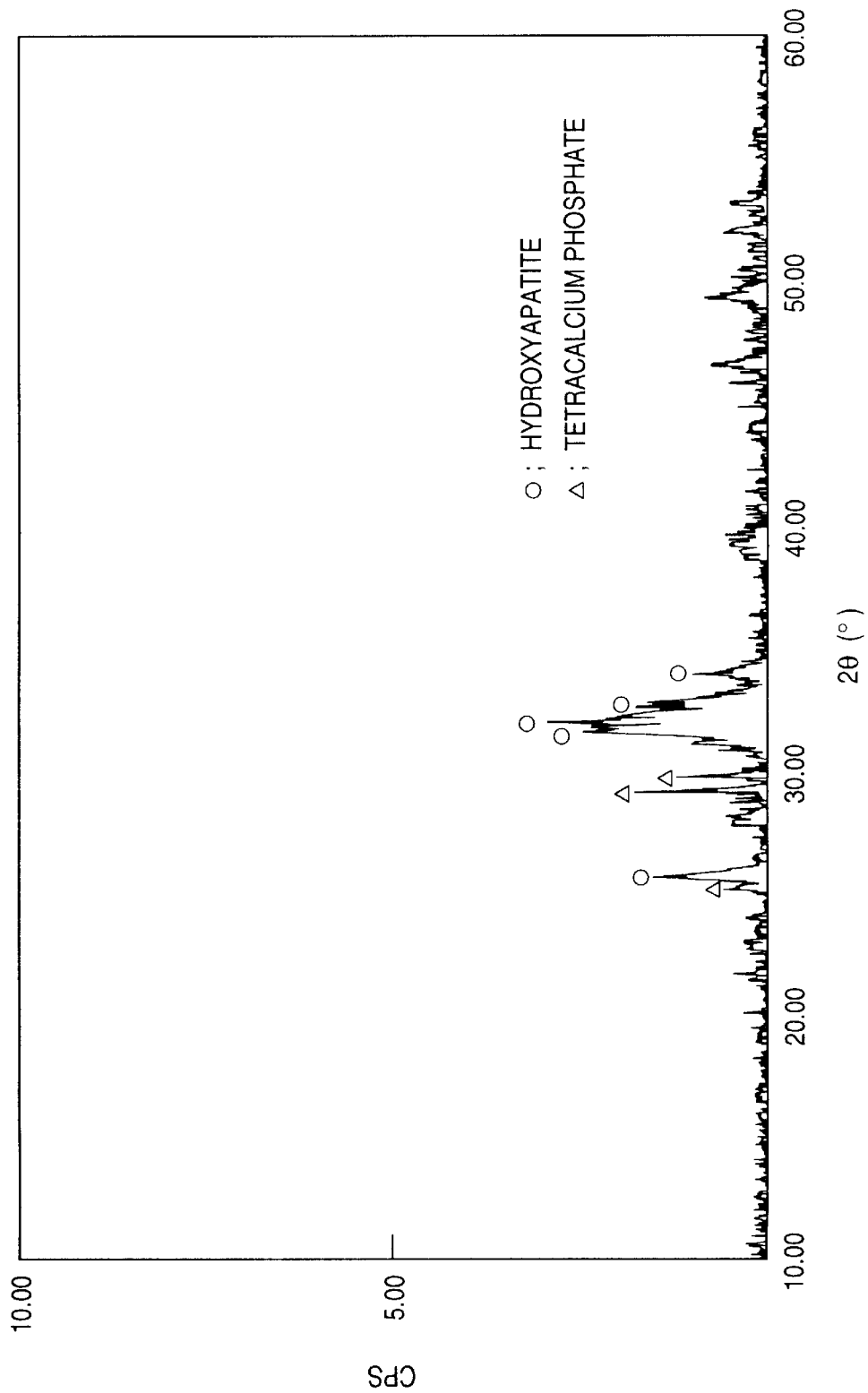
FIG. 1 is an X-ray diffractive chart of the hardened body obtained by hardening the kneaded body of the composition of EXPERIMENTAL EXAMPLE 5 under the conditions as described in EXPERIMENTAL EXAMPLE 24.

The calcium phosphate cement of a first embodiment according to the present invention comprises a calcium phosphate powder and a N-alkyl-D-glucamine wherein the alkyl means methyl, ethyl, n-propyl or isopropyl.

The calcium phosphate cement of a fourth embodiment according to the present invention comprises a calcium phosphate powder and at least one member selected from methanolamine, ethanolamine, n-propanolamine and isopropanolamine. This amine involves mono-, di- and triamines.

The calcium phosphate cement of an eighth embodiment according to the present invention comprises a calcium phosphate powder and a kneading liquid containing an N-alkyl-D-glucamine wherein the alkyl means methyl, ethyl, n-propyl or isopropyl.

The calcium phosphate cement composition of a tenth embodiment according to the present invention comprises a calcium phosphate powder and a kneading liquid containing at least one member selected from methanolamine, ethanolamine, n-propanolamine and isopropanolamine. This amine involves mono-, di- and triamines.

In the first and eighth embodiments of the present invention, the term "N-alkyl-D-glucamine" means a compound wherein the hydrogen at the N-position of D-glucamine is substituted by an alkyl group. In the first and eighth embodiments of the present invention, use can be made of compounds carrying a methyl, ethyl, n-propyl or isopropyl group as the alkyl substituent. Among these compounds, N-methyl-D-glucamine is particularly preferable therefor, since it has been proved as safe and nontoxic to living bodies and, therefore, used as a medical additive in X-ray contrast media. These compounds may be used alone or in combinations of two or more.

In the first embodiment according to the present invention, it is preferable that the N-alkyl-D-glucamine is used in an amount of "0.05 to 5 parts by weight" per 100 parts by weight of the above-mentioned "calcium phosphate cement", as stated in the second embodiment according to the present invention. When the content of the N-alkyl-D-glucamine is less than 0.05 parts by weight, it may be hard to obtain a kneaded body having sufficient handleability with the use of a kneading liquid at a low proportion. As a result, it is sometimes observed that voids are formed in the kneaded body after filling into a mold. On the other hand, it is not preferable that the content of the N-alkyl-D-glucamine exceeds 5 parts by weight. In this case, the handleability in the step of kneading may not be improved and thus the hardening time may not be satisfactorily shortened. It also may be hard in this case to elevate the strength of the hardened body. It is preferable that the content of the N-alkyl-D-glucamine is controlled to 0.1 to 4 parts by weight, still preferably from 0.5 to 3 parts by weight. When the content of the N-alkyl-D-glucamine falls within this scope, excellent handleability can be achieved in the kneading step and the kneaded body can be hardened within a short time to give a hardened body having a high strength.

Moreover, it is preferable that the N-alkyl-D-glucamine to be blended with the calcium phosphate powder has an average particle diameter of "0.1 to 100 μm". When the average particle diameter of the N-alkyl-D-glucamine is much less than 0.1 μm, the kneaded body has a low viscosity and shows only insufficiently improved shape-impartation. On the other hand, it is not preferable that the average particle diameter thereof exceeds 100 μm too much. In this case, the N-alkyl-D-glucamine can be hardly uniformly mixed with the calcium phosphate powder, which may make it impossible to give a kneaded body having excellent handleability, in particular, when a kneading liquid is used in a small amount. It is still preferable to control the average particle diameter of the N-alkyl-D-glucamine to 0.5 to 80 μm, in particular, 1 to 70 μm so as to fully improve the handleability of the kneaded body. The average particle diameter can be determined by a laser diffraction type particle size distribution analyzer (e.g., Type "LA-500", manufactured by Horiba Ltd.).

In the eighth embodiment according to the present invention, it is preferable that the N-alkyl-D-glucamine is used in an amount of "0.1 to 10 parts by weight" per 100 parts by weight of the kneading liquid, as stated in the ninth embodiment according to the present invention. When the content of the N-alkyl-D-glucamine is much less than 0.1 parts by weight, it may be impossible to obtain a kneaded body having a sufficient handleability with the use of a kneading liquid at a low proportion to the calcium phosphate powder. As a result, it is sometimes observed that voids are formed in the kneaded body after filling into a mold. On the other hand, it is not preferable that the content of the N-alkyl-D-glucamine exceeds 10 parts by weight too much. In this case, the handleabiliny in the step of kneading may not be improved and thus the hardening time cannot be satisfactorily shortened. It may be also impossible in this case to elevate the strength of the hardened body. It is preferable that the content of the N-alkyl-D-glucamine is controlled to 0.5 to 8 parts by weight, still preferably 1 to 7 parts by weight. When the content of the N-alkyl-D-glucamine falls within this scope, excellent handleability can be achieved in the kneading step and the kneaded body is hardened within a short time to give a hardened body having a high strength.

As the specific alkanolamine in the fourth and tenth embodiments of the present invention, use can be made of aliphatic alcohol amines having 1 to 3 carbon atoms. Although either a monoamine, a diamine or a triamine is usable therefor, it is preferable to employ a highly water-soluble amine, in particular, monoethanolamine which can be easily obtained. These alkanolamines may be used alone or in combinations of two or more.

In the fourth embodiment according to the present invention, it is preferable that the alkanolamine is used in an amount of 0.05 to 5 parts by weight, still preferably 0.1 to 4 parts by weight, per 100 parts by weight of the calcium phosphate cement. When a cement containing an amine in an amount as specified above is blended with an appropriate amount of a kneading liquid, the obtained mixture shows excellent handleability in the kneading step and the kneaded body can be hardened within a short time to give a hardened body having a high strength. In the tenth embodiment according to the present invention, it is preferable that the alkanolamine is used in an amount of 0.1 to 10 parts by weight, still preferably 0.5 to 8 parts by weight, per 100 parts by weight of the kneading liquid. When an appropriate amount of a kneading liquid containing an amine in an amount as specified above is blended with a calcium phosphate powder, the obtained mixture shows excellent handleability in the kneading step and the kneaded body can be hardened within a short time to give a hardened body having a high strength.

The calcium phosphate cements of the first and fourth embodiments according to the present invention can contain a "polysaccharide", as stated in the fifth embodiment thereof. By using a polysaccharide, the viscosity of the kneaded body can be appropriately elevated and thus the shape-impartation thereof can be improved. In the calcium phosphate cement compositions of the eighth and tenth embodiments according to the present invention, the kneading liquid contains a polysaccharide, as stated in the eleventh embodiment thereof. By using a polysaccharide, the viscosity of the kneading liquid can be appropriately elevated and thus a kneaded body having excellent shape-impartation can be obtained.

As the polysaccharide, use can be made of polymers formed from various monosaccharides through polyglycosyaltion. As stated in the sixth and twelfth embodiments according to the present invention, it is particularly preferable to use "dextran" or "dextran sulfate" therefor. More preferable examples of the dextran sulfate include dextran sulfate sodium and dextran sulfate potassium. Similar to the specific alkanolamines and N-alkyl-D-glucamine, these dextran and dextran sulfate are highly soluble in water. Thus, they are easily soluble in water which is the main component of the kneading liquid to give a uniform kneading liquid or kneaded body.

In the sixth embodiment according to the present invention, it is preferable to use 1 to 10 parts by weight, still preferably 2 to 8 parts by weight, of dextran, or to use 5 to 25 parts by weight, still preferably 10 to 20 parts by weight of dextran sulfate each per 100 parts by weight of the calcium phosphate cement. When the content of dextran or dextran sulfate is much less than the lower limit as specified above, the resultant kneaded body has a poor viscosity and can achieve little shape impartation. In this case, therefore, the effects of the use of dextran, etc. can be hardly established. When such a component is used in an amount close to the upper limit as specified above, on the other hand, the kneaded body can be sufficiently free from disintegration and the given shape can be retained. It is therefore unnecessary to use dextran or dextran sulfate exceeding this level any more. When the content thereof exceeds the upper limit, the kneaded body is liable to become too viscous, which may make shape impartation difficult.

In the twelfth embodiment according to the present invention, it is preferable to use 5 to 30 parts by weight, still preferably 10 to 25 parts by weight, of dextran, or to use 30 to 60 parts by weight, still preferably 35 to 55 parts by weight of dextran sulfate each per 100 parts by weight of the kneading liquid. When the content of dextran or dextran sulfate is much less than the lower limit as specified above, the resultant kneaded body has a poor viscosity and can achieve little shape impartation. In this case, therefore, the effects of the use of dextran, etc. can be hardly established. When such a component is used in an amount close to the upper limit as specified above, on the other hand, the kneaded body has an appropriate viscosity and thus a desired shape can be easily imparted thereto. It is therefore unnecessary to use dextran or dextran sulfate exceeding this level any more. When the content thereof exceeds the upper limit too much, the kneaded body is liable to become too viscous, which may make shape impartation difficult.

In the first and fourth embodiments according to the present invention, water is usable as the kneading liquid. It is also possible to use a combination of an amine-containing powder with water containing a polysaccharide such as dextran or dextran sulfate as the kneading liquid. In the eighth and tenth embodiments according to the present invention, on the other hand, an aqueous solution of amine is usable as the kneading liquid. As the water to be used in these cases, pure water is preferable in particular. The water may further contain an acid having been used in the art in kneading liquids of this type. As the acid, use may be made of either an organic acid (citric acid, etc.) or an inorganic acid (phosphoric acid, etc.). The content of the acid may range from 0.1 to 10 parts by weight, in particular, 0.5 to 8 parts by weight, per 100 parts by weight of the kneading liquid. When the content of the acid is too small, the hardening time cannot be sufficiently shortened. When the acid is used in excess, the hardening starts during kneading, thus deteriorating the handleability. When an acid is used, the pH value of a kneading liquid usually shifts toward the acidic region, thus causing inflammatory reactions around the application site in a living body. In the present invention, however, the pH value of the kneading liquid is maintained in the neutral region owing to the amine contained in the powder of the kneading liquid and, therefore, the above-mentioned troubles would never arise.

As the aforementioned "calcium phosphate powder", use can be made of powders of tetracalcium phosphate, calcium hydrogen phosphate, hydroxyapatite, tricalcium α-phosphate, tricalcium β-phosphate and the like. These powders may be used alone or in combinations of two or more. An X-ray contrast medium (e.g., barium sulfate, bismuth subcarbonate) may be incorporated into this powder. It is also possible to add a fluoride, or the like as seed crystals in order to reduce the hardening time.

A preferable calcium phosphate powder comprises powders of tetracalcium phosphate and calcium hydrogen phosphate as the main components as stated in the seventh and thirteenth embodiments according to the present invention. Although the proportions of these two powders are not particularly limited, the two powders are preferably used in a molar ratio of 8/2 to 2/8, still preferably about 6/4 to 4/6 and most desirably at the equimolar ratio. The term "main component" as used herein means that the aforesaid two powders are used in a total amount of 60 parts by weight or more, preferably 80 parts by weight or more, per 100 parts by weight of the whole calcium phosphate powder. Due to the combined use of these two powders as the main components, the kneading body scarcely undergoes disintegration and thus the given shape can be easily retained.

Processes for producing the tetracalcium phosphate powder are not particularly limited, and a powder produced by any process can be used. For example, use may be made of a powder produced by preparing an equimolar mixture of calcium carbonate and calcium hydrogen phosphate, molding the mixture into a given shape, sintering the shape at a temperature in the range of 1450 to 1550° C., and then pulverizing the sintered shape into a powder having an average particle diameter of about 100 μm. As the calcium hydrogen phosphate powder, on the other hand, a commercial product of either calcium hydrogen phosphate dihydrate or anhydrous calcium hydrogen phosphate can be used in its commercial form. It is also possible to use a powder obtained by dehydrating the commercial dihydrate by heating it at about 120° C. However, the calcium hydrogen phosphate powder for use in the present invention should not be construed as being limited to these powders.

The viscosity of the kneaded body comprising the powder and the kneading liquid can be regulated by controlling the proportions of these components. In the first to seventh embodiments according to the present invention, the proportion of the kneading liquid can be lowered so as to give a kneaded body having a viscosity comparable to the one obtained by using a cement comprising a calcium phosphate powder alone. In the eighth to thirteenth embodiments according to the present invention, on the other hand, the proportion of the kneading liquid can be lowered so as to give a kneaded body having a viscosity comparable to the one obtained by using a kneading liquid comprising pure water alone. In the present invention, therefore, the hardening time can be shortened and a hardened body with an elevated strength can be obtained. That is, the hardening time measured in accordance to JIS T 6602 can be reduced to 10 to 25 minutes, in particular, 10 to 20 minutes, while the wet compressive strength can be elevated to 500 to 700 kg/cm$^2$, in particular 600 to 700 kg/cm$^2$.

With respect to the proportions of the powder and the kneading liquid, it is preferable to use 10 to 25 parts by weight, still preferably 15 to 25 parts by weight and particularly preferably 20 parts by weight, of the kneading liquid per 100 parts by weight of the powder. In the present invention, the proportion of the kneading liquid can be reduced as described above. When the proportion is too low, however, the viscosity of the kneaded body becomes too high and thus it is difficult to impart a given shape. When the proportion of the kneading liquid is too high, on the other hand, the kneaded body becomes less viscous and can be easily handled. However, it is not preferable since a long hardening time is needed and the strength of the hardened body is deteriorated in this case.

Kneaded bodies prepared with the use of the calcium phosphate cements or calcium phosphate cement compositions according to the present invention can be employed in vivo applications such as artificial bones, artificial tooth roots, etc. Furthermore, it is also possible to add bone-forming factors, antitumor agents, antibiotics, etc. during the kneading step to thereby use the hardened cements as carriers for gradual drug release.

The calcium phosphate cements of the first and fourth embodiments according to the present invention contain an appropriate amount of an N-alkyl-D-glucamine or a specific alkanolamine. In the calcium phosphate cement compositions of the eighth and tenth embodiments according to the present invention, use is made as a kneading liquid of an aqueous solution containing an appropriate amount of an N-alkyl-D-glucamine or a specific alkanolamine. When the cement of the first or fourth embodiment according to the present invention is kneaded with the use of a kneading liquid containing water as the main component, or when a calcium phosphate powder is kneaded by using the calcium phosphate cement composition of the eighth or tenth embodiment according to the present invention, the N-alkyl- D-glucamine, etc. and water penetrate among the calcium phosphate particles having aggregated together and thus disperse the particles. Since the powder particles are thus easily dispersed, the viscosity of the resultant kneaded body is not so elevated even though the kneading liquid is used in a small amount, thus achieving excellent handleability in the kneading step. By somewhat increasing the proportion of the kneading liquid, the viscosity of the kneaded body can be further lowered. Consequently, the kneaded body can be easily filled into a bone defective site, a bone fracture site and the like by using a syringe, etc. Thus, the load to a patient can be relieved.

In the calcium phosphate cements of the fifth and sixth embodiments according to the present invention, a polysaccharide such as dextran or dextran sulfate can be used in an appropriate amount together with an amine. In the calcium phosphate cement compositions of the eleventh and twelfth embodiments according to the present invention, furthermore, a kneading liquid may contain an appropriate amount of a polysaccharide such as dextran or dextran sulfate in addition to an amine. Because of having an effect of adhering calcium phosphate powder particles, which have been dispersed, to each other, these polysaccharides contribute to the regulation of the viscosity of the kneaded body. Thus, a kneaded body showing excellent shape-impartation can be obtained by using the kneading liquid in a reduced amount. The term "shape-impartation" as used herein means both of the impartation of an initial shape and the correction and modification into the given shape after the application, etc.

Examples of the present invention will be given below.
(I) Addition of Specific Compound to Calcium Phosphate Powder In EXPERIMENTAL EXAMPLES 1 to 21, an equimolar mixture of a tetracalcium phosphate powder and an anhydrous calcium hydrogen phosphate powder was used as a calcium phosphate powder.
(1) EXPERIMENTAL EXAMPLES with the use of cements containing N-alkyl-D-glucamine or alkanolamine (In EXPERIMENTAL EXAMPLES 1 to 7, cements comprising a calcium phosphate powder alone were employed.):

EXPERIMENTAL EXAMPLE 1

As a cement, use was made of a calcium phosphate powder alone. To this cement, pure water was added as a kneading liquid so as to give a weight ratio of the pure water to the cement (hereinafter the weight ratio of kneading liquid/cement will be referred to as L/P) of 0.21 followed by kneading. The resultant kneaded body had a high viscosity. When it was filled into a mold and hardened, the hardened body had number of voids. Although it was attempted to carry out the kneading at an L/P of 0.19, no kneading could be achieved due to the insufficient amount of pure water.

EXPERIMENTAL EXAMPLE 2

A calcium phosphate powder and 0.02 parts by weight of N-methyl-D-glucamine (manufactured by Sigma, average particle diameter=0.5 $\mu$m) were mixed in a ball mill to give a cement. Although it was attempted to knead the thus obtained cement as in EXPERIMENTAL EXAMPLE 1, kneading could be hardly effected at this L/P due to the insufficient amount of pure water.

EXPERIMENTAL EXAMPLE 3

A cement containing 0.1 part by weight of N-methyl-D-glucamine (average particle diameter=10 $\mu$m) was kneaded at an L/P of 0.19 as in EXPERIMENTAL EXAMPLE 2. As a result, the resultant kneaded body could be easily filled into a mold and showed excellent handleability. The hardened body thus obtained had no void.

EXPERIMENTAL EXAMPLE 4

A cement containing 2 parts by weight of N-methyl-D-glucamine (average particle diameter=50 $\mu$m) was kneaded at an L/P of 0.17 as in EXPERIMENTAL EXAMPLE 2. As a result, the resultant kneaded body could be easily filled into a mold and showed excellent handleability. The hardened body thus obtained had no void.

EXPERIMENTAL EXAMPLE 5

A cement containing 5 parts by weight of N-methyl-D-glucamine (average particle diameter=30 $\mu$m) was kneaded as in EXPERIMENTAL EXAMPLE 4. As a result, the resultant kneaded body could be easily filled into a mold and showed excellent handleability. The hardened body thus obtained had no void.

EXPERIMENTAL EXAMPLE 6

A cement containing 6 parts by weight of N-methyl-D-glucamine (average particle diameter=10 $\mu$m) was kneaded as in EXPERIMENTAL EXAMPLE 4. As a result, the resultant kneaded body could be easily filled into a mold and showed excellent handleability. The hardened body thus obtained had no void. However, a long hardening time was required in this case.

EXPERIMENTAL EXAMPLE 7

Kneading was effected as in EXPERIMENTAL EXAMPLE 1 but at an L/P of 0.29. The kneaded body thus obtained had a low viscosity and thus could be extruded with an 18-gage syringe. It could be easily filled into a mold and showed excellent handleability. The hardened body thus obtained had no void. However, it had a poor compressive strength and easily disintegrated. When the L/P was lowered to 0.25, the kneaded body could not be extruded with a syringe due to an increase in the viscosity.

EXPERIMENTAL EXAMPLE 8

A cement containing 2 parts by weight of N-methyl-D-glucamine (average particle diameter=30 $\mu$m) was kneaded at an L/P of 0.25 as in EXPERIMENTAL EXAMPLE 2. The kneaded body thus obtained had a low viscosity and thus could be extruded with an 18-gage syringe. It could be easily filled into a mold and showed excellent handleability. The hardened body thus obtained had no void.

EXPERIMENTAL EXAMPLE 9

Although it was attempted to knead a cement prepared by mixing a calcium phosphate powder with 0.02 parts by weight of monoethanolamine as in EXPERIMENTAL EXAMPLE 2, kneading could be hardly effected at this L/P due to the insufficient amount of pure water.

EXPERIMENTAL EXAMPLE 10

A cement containing 1 part by weight of monoethanolamine was kneaded at an L/P of 0.19 as in EXPERIMENTAL EXAMPLE 9. The kneaded body thus obtained could be easily filled into a mold and showed excellent handleability. The hardened body thus obtained had no void.
(2) EXPERIMENTAL EXAMPLES with the use of cements containing n-alkyl-D-glucamine and polysaccharide:

EXPERIMENTAL EXAMPLE 11

A cement containing 3 parts by weight of N-methyl-D-glucamine (average particle diameter=20 μm) and 0.5 parts by weight of Dextran 40 (average molecular weight=40,000; manufactured by Meito Sangyo K.K.) was kneaded at an L/P of 0.19 as in EXPERIMENTAL EXAMPLE 2. As a result, the resultant kneaded body could be easily filled into a mold and showed excellent handleability. The hardened body thus obtained had no void and showed excellent shape impartation.

EXPERIMENTAL EXAMPLE 12

Kneading was effected as in EXPERIMENTAL EXAMPLE 11 but using 5 parts by weight of Dextran 40. As a result, the resultant kneaded body could be easily filled into a mold and showed excellent handleability. The hardened body thus obtained had no void and showed excellent shape impartation.

EXPERIMENTAL EXAMPLE 13

Kneading was effected as in EXPERIMENTAL EXAMPLE 11 but using 12 parts by weight of Dextran 40. As a result, the resultant kneaded body could be easily filled into a mold and showed excellent handleability. The hardened body thus obtained had no void and showed excellent shape impartation.

EXPERIMENTAL EXAMPLE 14

A cement containing 2 parts by weight of N-methyl-D-glucamine and 15 parts by weight of Dextran sulfate sodium sulfur 5 (average molecular weight=2,000; manufactured by Metro Sangyo K.K.) was kneaded as in EXPERIMENTAL EXAMPLE 11. As a result, a paste which had an appropriate viscosity and could be shaped into a desired form was obtained. It could be easily filled into a mold. The hardened body thus obtained had no void.

(3) EXPERIMENTAL EXAMPLES with the use of cements containing n-alkyl-D-glucamine and kneading liquids containing polysaccharides:

EXPERIMENTAL EXAMPLE 15

A calcium phosphate cement composition comprising the cement of EXPERIMENTAL EXAMPLE 3 and a kneading liquid prepared by dissolving 3 parts by weight of Dextran 40 in pure water was kneaded at an L/P of 0.19 as in EXPERIMENTAL EXAMPLE 2. As a result, the resultant kneaded body could be easily filled into a mold and showed excellent handleability. The hardened body thus obtained had no void and showed an excellent shape impartation.

EXPERIMENTAL EXAMPLE 16

Kneading was effected as in EXPERIMENTAL EXAMPLE 15 but using 20 parts by weight of Dextran 40. As a result, the resultant kneaded body could be easily filled into a mold and showed excellent handleability. The hardened body thus obtained had no void and showed excellent shape impartation.

EXPERIMENTAL EXAMPLE 17

Kneading was effected as in EXPERIMENTAL EXAMPLE 15 but using 35 parts by weight of Dextran 40. As a result, the resultant kneaded body could be easily filled into a mold and showed excellent handleability. The hardened body thus obtained had no void and showed excellent shape impartation.

EXPERIMENTAL EXAMPLE 18

Kneading was effected as in EXPERIMENTAL EXAMPLE 15 but using a cement comprising n-alkyl-D-glucamine and 20 parts by weight of Dextran sulfate sodium sulfur. As a result, the resultant kneaded body could be easily filled into a mold and showed excellent handleability. The hardened body thus obtained had no void and showed excellent shape impartation.

(4) EXPERIMENTAL EXAMPLES with the use of cements containing n-alkyl-D-glucamine and kneading liquids containing polysaccharides and acids

EXPERIMENTAL EXAMPLE 19

A calcium phosphate cement composition comprising a cement containing 0.5 parts by weight of N-methyl-D-glucamine (average particle diameter=10 μm) and a kneading liquid prepared by dissolving 15 parts by weight of Dextran 40 and 0.3 parts by weight of citric acid (monohydrate, manufactured by Hayashi Junyaku K.K.) in pure water was kneaded at an L/P of 0.19 as in EXPERIMENTAL EXAMPLE 2. As a result, the resultant kneaded body could be easily filled into a mold and showed excellent handleability. The hardened body thus obtained had no void.

EXPERIMENTAL EXAMPLE 20

Kneading was effected as in EXPERIMENTAL EXAMPLE 19 but using 1 part by weight of citric acid. As a result, the resultant kneaded body could be easily filled into a mold and showed excellent handleability. The hardened body thus obtained had no void.

EXPERIMENTAL EXAMPLE 21

Kneading was effected as in EXPERIMENTAL EXAMPLE 19 but using 12 parts by weight of citric acid. As a result, the resultant kneaded body could be easily filled into a mold and showed excellent handleability. The hardened body thus obtained had no void.

EXPERIMENTAL EXAMPLE 22

The kneaded bodies prepared in EXPERIMENTAL EXAMPLES 1 to 21 were evaluated for hardening time and wet compressive strength in accordance with JIS T 6602.

EXPERIMENTAL EXAMPLE 23

The kneaded bodies prepared in EXPERIMENTAL EXAMPLES 1 to 10 were molded by packing into a mold having a cavity with an inner diameter of 6 mm and a depth of 5 mm. Each molded article was taken out of the mold and immediately immersed in a pseudo body fluid at 37° C. to evaluate its tolerance to disintegration.

Tables 1 and 2 summarize the results of the evaluation for hardening time, wet compressive strength and tolerance to disintegration. Tables 1 and 2 also show the data on handleability and filling performance of the samples of EXPERIMENTAL EXAMPLES 1 to 21 and the data on shape impartation of the samples of EXPERIMENTAL EXAMPLES 1 to 18.

EXPERIMENTAL EXAMPLE 24

The kneaded bodies prepared in EXPERIMENTAL EXAMPLES 1 to 21 were hardened in an atmosphere at a temperature of 37° C. under a relative humidity of 100%. The hardening was continued for 1 hour after the initiation of kneading. Each hardened body thus obtained was immersed in a pseudo body fluid at 37° C. for 23 hours and then its structural crystalline phase was analyzed by X-ray diffractometry. As a result, diffraction peaks assignable to hydroxyapatite and tetracalcium phosphate were observed in each of the samples of EXPERIMENTAL EXAMPLES 1 to 21. FIG. 1 shows the X-ray diffraction chart of the hardened body obtained by hardening the kneaded body of EXPERIMENTAL EXAMPLE 5.

N-methyl-D-glucamine in an amount exceeding the upper limit of the second embodiment according to the present invention, the hardening time was considerably prolonged. In EXPERIMENTAL EXAMPLE 7 with the use of the cement comprising a calcium phosphate powder alone and an elevated L/P, the hardening time was prolonged and the compressive strength was lowered.

TABLE 1

| Ex. no. | Additives in powder (part) | MEG particle size (μm) | L/P | Handle-ability | Filling performance | Hardening time (min) | Compressive strength (kg/cm$^2$) | Tolerance to disintegration | Shape impartation |
|---|---|---|---|---|---|---|---|---|---|
| 1 | — | — | 0.21 | x | x | 21 | 480 | x | — |
| 2 | MEG/0.02 | 0.5 | | Δ | Δ | 24 | 450 | Δ | |
| 3 | MEG/0.1 | 10 | 0.19 | ○ | ○ | 18 | 580 | ○ | |
| 4 | MEG/2 | 50 | 0.17 | | | 13 | 610 | | |
| 5 | MEG/5 | 30 | | | | 10 | 660 | | |
| 6 | MEG/6 | 10 | | | | 46 | 460 | | |
| 7 | — | — | 0.29 | | | 33 | 350 | x | |
| 8 | MEG/2 | 30 | 0.25 | | | 23 | 500 | ○ | |
| 9 | MEA/0.02 | — | 0.21 | Δ | Δ | 22 | 430 | Δ | |
| 10 | MEA/1 | — | 0.19 | ○ | ○ | 15 | 640 | ○ | |
| 11 | MEG/3 + DEX/0.5 | 20 | | ○ | ○ | 17 | 630 | — | ○ |
| 12 | MEG/3 + DEX/5 | | | | | 16 | 620 | | ◎ |
| 13 | MEG/3 + DEX/12 | | | | | 14 | 650 | | ○ |
| 14 | MEG/2 + DSS/15 | | | | | 18 | 610 | | ◎ |

TABLE 2

| | Additives in powder (part) | Additives in kneading liquid (part) | Handle-ability | Filling performance | Hardening time (min) | Compressive strength (kg/cm$^2$) | shape impartation |
|---|---|---|---|---|---|---|---|
| 15 | MEG/0.1 | DEX/3 | ○ | ○ | 17 | 610 | ○ |
| 16 | | DEX/20 | | | 19 | 580 | ◎ |
| 17 | | DEX/35 | | | 16 | 620 | ○ |
| 18 | | DSS/20 | | | 14 | 630 | ◎ |
| 19 | MEG/0.5 | DEX/15 + citric acid/0.3 | | | 16 | | — |
| 29 | | DEX/15 + citric acid/1 | | | 7 | 660 | |
| 21 | | DEX/15 + citric acid/12 | | | 2 | 670 | |

In each case, MEG had a particle size of 10 μm and L/P was 0.19.

① Results of Evaluation on EXPERIMENTAL EXAMPLES in the Category (1):

In EXPERIMENTAL EXAMPLES 3 to 5 and 8 with the use of the cements wherein the content or average particle diameter of N-methyl-D-glucamine fell within the scope of the present invention and in EXPERIMENTAL EXAMPLE 10 with the use of the cement containing an appropriate amount of monoethanolamine, excellent handleability and filling performance were achieved. In each of these cases, moreover, a short hardening time (23 minutes or less) and a high compressive strength (500 kg/cm$^2$ or more) were observed.

On the other hand, in EXPERIMENTAL EXAMPLE 1 with the use of the cement comprising a calcium phosphate powder alone, in EXPERIMENTAL EXAMPLE 2 with the use of N-methyl-D-glucamine in an amount less than the lower limit as specified in the second embodiment according to the present invention, and in EXPERIMENTAL EXAMPLE 9 with the use of an excessively small amount of monoethanolamine, the compressive strength was tend to decrease, though any serious problem was observed in neither handleability, filling performance nor hardening time. In EXPERIMENTAL EXAMPLE 6 with use of In EXPERIMENTAL EXAMPLES 3 to 6, 8 and 10, it was confirmed that each molded body was hardened while retaining its shape without disintegration. In EXPERIMENTAL EXAMPLES 1 and 7 with the use of the cements comprising a calcium phosphate powder alone, on the other hand, each molded body underwent disintegration and thus failed to retain its shape. In EXPERIMENTAL EXAMPLE 2 with the use of N-methyl-D-glucamine in an amount an amount less than the lower limit as specified in the second embodiment according to the present invention, and in EXPERIMENTAL EXAMPLE 9 with the use of an excessively small amount of monoethanolamine, each molded body showed a tendency toward disintegration.

② Results of Evaluation on EXPERIMENTAL EXAMPLES in the Category (2):

In EXPERIMENTAL EXAMPLES 11 to 14 with the use of the cements containing N-methyl-D-glucamine together with Dextran 40 or Dextran sulfur 5, hardening times were short (14 to 18 minutes) while compressive strengths were large (610 kg/cm$^2$ or more). In these cases, excellent handleability and filling performance were achieved and no serious problem was observed in shape impartation.

③ Results of Evaluation on EXPERIMENTAL EXAMPLES in the Category (3):

In EXPERIMENTAL EXAMPLES 15 to 18 with the use of the kneading liquids containing N-methyl-D-glucamine together with Dextran 40 or Dextran sulfur 5, hardening times were short (14 to 19 minutes) while compressive strengths were large (580 kg/cm$^2$ or more). In these cases, excellent handleability and filling performance were achieved and no serious problem was observed in shape impartation.

④ Results of Evaluation on EXPERIMENTAL EXAMPLES in the Category (4):

In EXPERIMENTAL EXAMPLES 19 to 21 with the use of the kneading liquids containing N-methyl-D-glucamine together with Dextran 40 and citric acid, hardening times were further short (2 to 16 minutes) while compressive strengths were further large (630 kg/cm$^2$ or more). In these cases, excellent handleability and filling performance were achieved and no serious problem was observed in shape impartation.

(II) Addition of Specific Compound to Kneading Liquid

In EXPERIMENTAL EXAMPLES 25 to 43, an equimolar mixture of a tetracalcium phosphate powder and an anhydrous calcium hydrogen phosphate powder was used as a calcium phosphate powder.

(1) EXPERIMENTAL EXAMPLES with the use of kneading liquids containing N-alkyl-D-glucamine or alkanolamine:

EXPERIMENTAL EXAMPLE 25

0.05 parts by weight of N-methyl-D-glucamine was dissolved in pure water and the kneading liquid thus prepared was kneaded together with a calcium phosphate powder as an L/P of 0.21. The resultant kneaded body had a high viscosity and somewhat poor handleability. This kneaded body was filled into a mold and hardened. The obtained hardened body had voids.

EXPERIMENTAL EXAMPLE 26

Kneading was effected as in EXPERIMENTAL EXAMPLE 25 but using 0.1 part by weight of N-methyl-D-glucamine. The resultant kneaded body showed excellent handleability and could be easily filled into a mold. After hardening, the hardened body had no void.

EXPERIMENTAL EXAMPLE 27

Kneading was effected as in EXPERIMENTAL EXAMPLE 25 but using 1 part by weight of N-methyl-D-glucamine at an L/P of 0.19. The resultant kneaded body showed excellent handleability and could be easily filled into a mold. After hardening, the hardened body had no void.

EXPERIMENTAL EXAMPLE 28

Kneading was effected as in EXPERIMENTAL EXAMPLE 25 but using 5 parts by weight of N-methyl-D-glucamine at an L/P of 0.17. The resultant kneaded body showed excellent handleability and could be easily filled into a mold. After hardening, the hardened body had no void.

EXPERIMENTAL EXAMPLE 29

Kneading was effected as in EXPERIMENTAL EXAMPLE 25 but using 15 parts by weight of N-methyl-D-glucamine at an L/P of 0.17. The resultant kneaded body showed excellent handleability and could be easily filled into a mold. After hardening, the hardened body had no void. However, a somewhat long time was required in hardening.

EXPERIMENTAL EXAMPLE 30

Kneading was effected as in EXPERIMENTAL EXAMPLE 25 but using 10 part by weight of N-methyl-D-glucamine at an L/P of 0.23. The resultant kneaded body had a low viscosity and could be extruded with an 18-gage syringe.

EXPERIMENTAL EXAMPLE 31

Kneading was effected as in EXPERIMENTAL EXAMPLE 25 but using a kneading liquid prepared by dissolving 0.05 parts by weight of monoethanolamine in pure water at an L/P of 0.19. The resultant kneaded body had a high viscosity and somewhat poor handleability. When it was filled in a mold and hardened therein, the obtained hardened body had voids.

EXPERIMENTAL EXAMPLE 32

Kneading was effected as in EXPERIMENTAL EXAMPLE 31 but using 2 parts by weight of monoethanolamine at an L/P of 0.19. The resultant kneaded body had excellent handleability and could be easily filled into a mold. After hardening, the obtained hardened body had no void.

(2) EXPERIMENTAL EXAMPLES with the use of kneading liquids containing N-alkyl-D-glucamine and polysaccharide:

EXPERIMENTAL EXAMPLE 33

Kneading was effected as in EXPERIMENTAL EXAMPLE 25 but using a kneading liquid containing 3 parts by weight of N-methyl-D-glucamine and 3 parts by weight of Dextran 40 at an L/P of 0.19. The resultant kneaded body could be easily filled into a mold and showed excellent handleability. After hardening, the obtained hardened body had no void and showed excellent shape impartation.

EXPERIMENTAL EXAMPLE 34

Kneading was effected as in EXPERIMENTAL EXAMPLE 33 but using 2 parts by weight of N-methyl-D-glucamine and 15 parts by weight of Dextran 40. The resultant kneaded body could be easily filled into a mold and showed excellent handleability. After hardening, the obtained hardened body had no void and showed excellent shape impartation.

EXPERIMENTAL EXAMPLE 35

Kneading was effected as in EXPERIMENTAL EXAMPLE 33 but using 35 parts by weight of Dextran 40. The resultant kneaded body could be easily filled into a mold and showed excellent handleability. After hardening, the obtained hardened body had no void and showed excellent shape impartation.

EXPERIMENTAL EXAMPLE 36

Kneading was effected as in EXPERIMENTAL EXAMPLE 33 but using a kneading liquid containing 2 parts by weight of N-methyl-D-glucamine and 50 parts by weight of Dextran sulfate sodium sulfur 5. The resultant kneaded body could be easily filled into a mold and showed excellent handleability. After hardening, the obtained hardened body had no void and showed excellent shape impartation.

(3) EXPERIMENTAL EXAMPLES with the use of kneading liquids containing N-alkyl-D-glucamine, polysaccharide and acid:

EXPERIMENTAL EXAMPLE 37

Kneading was effected as in EXPERIMENTAL EXAMPLE 25 but using a kneading liquid prepared by dissolving 3 parts by weight N-methyl-D-glucamine, 20 parts by weight of Dextran 40 and 0.3 parts by weight of citric acid in pure water. The resultant kneaded body could be easily filled into a mold and showed excellent handleability. After hardening, the obtained hardened body had no void. The kneading liquid had a pH value of 9.4.

EXPERIMENTAL EXAMPLE 38

Kneading was effected as in EXPERIMENTAL EXAMPLE 37 but using 25 parts by weight of Dextran 40 and 2 parts by weight of citric acid. The resultant kneaded body could be easily filled into a mold and showed excellent handleability. After hardening, the obtained hardened body had no void. The kneading liquid had a pH value of 6.3.

EXPERIMENTAL EXAMPLE 39

A calcium phosphate powder was kneaded as in EXPERIMENTAL EXAMPLE 37 but using 20 parts by weight of Dextran 40 and 12 parts by weight of citric acid. The resultant kneaded body could be easily filled into a mold and showed excellent handleability. After hardening, the obtained hardened body had no void. The kneading liquid had a pH value of 5.2.

EXPERIMENTAL EXAMPLE 40

Kneading was effected as in EXPERIMENTAL EXAMPLE 37 but using 2 parts by weight of N-methyl-D-glucamine, 10 parts by weight of Dextran 40 and 0.2 parts by weight of citric acid. The resultant kneaded body could be easily filled into a mold and showed excellent handleability. After hardening, the obtained hardened body had no void. The kneading liquid had a pH value of 8.5.

EXPERIMENTAL EXAMPLE 41

Kneading was effected as in EXPERIMENTAL EXAMPLE 40 but using 1 part by weight of citric acid. The resultant kneaded body could be easily filled into a mold and showed excellent handleability. After hardening, the obtained hardened body had no void. The kneading liquid had a pH value of 6.8.

EXPERIMENTAL EXAMPLE 42

Kneading was effected as in EXPERIMENTAL EXAMPLE 40 but using 11 parts by weight of citric acid. The resultant kneaded body could be easily filled into a mold and showed excellent handleability. After hardening, the obtained hardened body had no void. The kneading liquid had a pH value of 5.9.

EXPERIMENTAL EXAMPLE 43

Kneading was effected as in EXPERIMENTAL EXAMPLE 40 but using a kneading liquid containing N-methyl-D-glucamine, 50 parts by weight of Dextran sulfate sodium sulfur 5 and 4 parts by weight of citric acid. The resultant kneaded body could be easily filled into a mold and showed excellent handleability. After hardening, the obtained hardened body had no void. The kneading liquid had a pH value of 6.4.

EXPERIMENTAL EXAMPLE 44

The kneaded bodies prepared in EXPERIMENTAL EXAMPLES 25 to 43 were examined for wet compressive strength in accordance with JIS T 6602.

EXPERIMENTAL EXAMPLE 45

The kneaded bodies prepared in EXPERIMENTAL EXAMPLES 25 to 32 were molded by packing into a mold having a cavity with an inner diameter of 6 mm and a depth of 5 mm. Each molded article was taken out of the mold and immediately immersed in a pseudo body fluid at 37° C.

Tables 3 and 4 summarize the results of the evaluation for hardening time, wet compressive strength and tolerance to disintegration. Tables 3 and 4 also show the data on handleability and filling performance of the samples of EXPERIMENTAL EXAMPLES 25 to 43 and the data on shape impartation of the samples of EXPERIMENTAL EXAMPLES 33 to 36.

EXPERIMENTAL EXAMPLE 46

Figure 2:
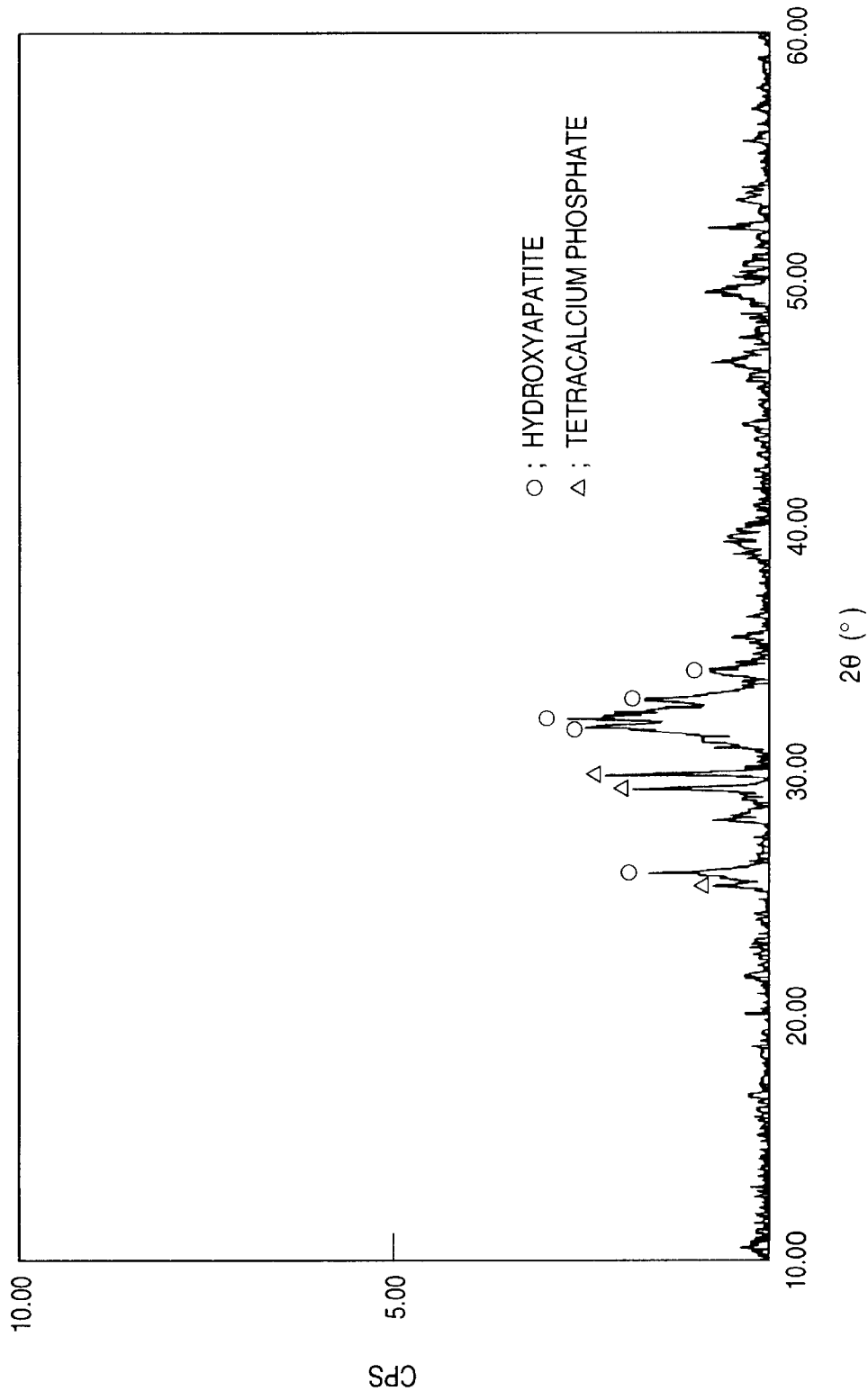
FIG. 2 is an X-ray diffractive chart of the hardened body obtained by hardening the kneaded body of the composition of EXPERIMENTAL EXAMPLE 28 under the conditions as described in EXPERIMENTAL EXAMPLE 46.

The kneaded bodies prepared in EXPERIMENTAL EXAMPLE 25 to 43 were hardened in an atmosphere at a temperature of 37° C. under a relative humidity of 100%. The hardening was continued for 1 hour after the initiation of kneading. Each hardened body thus obtained was immersed in a pseudo body fluid at 37° C. for 23 hours and then its structural crystalline phase was analyzed by X-ray diffractometry. As a result, diffraction peaks assignable to hydroxyapatite and tetracalcium phosphate were observed in each of the samples of EXPERIMENTAL EXAMPLES 25 to 43. FIG. 2 shows the X-ray diffraction chart of the hardened body obtained by hardening the kneaded body of EXPERIMENTAL EXAMPLE 28.

TABLE 3

| Ex. no. | Additives in kneading liquid (part) | L/P | Handle-ability | Filling performance | Hardening time (min) | Compressive strength (kg/cm$^2$) | Tolerance to disintegration | Shape impartation |
|---|---|---|---|---|---|---|---|---|
| 1 | pure water | 0.21 | x | x | 21 | 480 | x | — |
| 25 | MEG/0.05 | | Δ | Δ | 22 | 460 | Δ | |
| 26 | MEG/0.1 | | ○ | ○ | 19 | 550 | ○ | |
| 27 | MEG/1 | 0.19 | | | 16 | 620 | | |
| 28 | MEG/5 | 0.17 | | | 11 | 650 | | |
| 29 | MEG/15 | | | | 31 | 330 | | |
| 7 | — | 0.29 | | | 33 | 350 | x | |
| 30 | MEG/10 | 0.23 | | | 24 | 520 | ○ | |
| 31 | MEA/0.05 | 0.19 | Δ | Δ | 23 | 420 | Δ | |
| 32 | MEA/2 | | | | 17 | 610 | ○ | |
| 33 | MEG/3 + DEX/3 | 0.19 | ○ | ○ | 18 | 620 | — | ○ |
| 34 | MEG/2 + DEX/15 | | | | 19 | 670 | | ⊚ |
| 35 | MEG/3 + DEX/35 | | | | 17 | 650 | | ○ |
| 36 | MEG/2 + DSS/50 | | | | | 600 | | ⊚ |

TABLE 4

| Ex. no. | Additives in kneading liquid (part) | pH | L/P | Handle-ability | Filling performance | Hardening time (min) | Compressive strength (kg/cm²) |
|---|---|---|---|---|---|---|---|
| 37 | MEG/3 + DEX/20 + citric acid/0.3 | 9.4 | 0.21 | ○ | ○ | 19 | 690 |
| 38 | MEG/3 + DEX/25 + citric acid/2 | 6.3 | | | | 7 | |
| 39 | MEG/3 + DEX/20 + citric acid/12 | 5.2 | | | | 2 | 650 |
| 40 | MEG/2 + DEX/10 + citric acid/0.2 | 8.5 | 0.25 | | | 23 | 570 |
| 41 | MEG/2 + DEX/10 + citric acid/1 | 6.8 | | | | 19 | 540 |
| 42 | MEG/2 + DEX/10 + citric acid/11 | 5.9 | | | | 3 | 530 |
| 43 | MEG/2 + DSS/50 + citric acid/1 | 6.4 | 0.21 | | | 8 | 630 |

① Results of Evaluation on EXPERIMENTAL EXAMPLES in the Category (1):

In EXPERIMENTAL EXAMPLES 26 to 28 with the use of the kneading liquids containing N-methyl-D-glucamine in the amounts falling within the scope of the ninth embodiment according to the present invention and in EXPERIMENTAL EXAMPLE 32 with the use of the kneading liquid containing an appropriate amount of monoethanolamine, excellent handleability and filling performance were achieved. In each of these cases, moreover, a short hardening time (24 minutes or less) and a high compressive strength (520 kg/cm² or more) were observed.

On the other hand, in EXPERIMENTAL EXAMPLE 25 with the use of N-methyl-D-glucamine in an amount less than the lower limit as specified in the ninth embodiment according to the present invention and in EXPERIMENTAL EXAMPLE 31 with the use of an excessively small amount of monoethanolamine, the handleability and filling performance were poor and the compressive strength was liable to be lowered, though no problem was observed with respect to shortening time. In EXPERIMENTAL EXAMPLE 29 with the use of N-methyl-D-glucamine in an amount exceeding the upper limit as specified in the ninth embodiment according to the present invention, a prolonged hardening time was required.

In EXPERIMENTAL EXAMPLES 26 to 29, 30 and 32, each molded article was hardened while sustaining its shape without deterioration. In EXPERIMENTAL EXAMPLE 25 with the use of N-methyl-D-glucamine in an amount less than the lower limit as specified in the ninth embodiment according to the present invention and in EXPERIMENTAL EXAMPLE 31 with the use of an excessively small amount of monoethanolamine, the molded articles were liable to disintegrate.

② Results of Evaluation on EXPERIMENTAL EXAMPLES in the Category (2):

In EXPERIMENTAL EXAMPLES 33 to 36 with the use of the kneading liquids containing N-methyl-D-glucamine and Dextran 40 or Dextran sulfur 5, hardening times were short (17 to 19 minutes) and high compressive strengths (600 kg/cm² or more) were observed. Also, excellent handleability and filling performance were achieved and no problem was observed in shape impartation.

③ Results of Evaluation on EXPERIMENTAL EXAMPLES in the Category (3):

In EXPERIMENTAL EXAMPLES 37 to 43 with the use of the kneading liquids containing N-methyl-D-glucamine and Dextran 40 or Dextran sulfur 5 and citric acid, hardening times were shortened (2 to 23 minutes) and compressive strengths were elevated (530 kg/cm² or more). It was also understood that excellent handleability and filling performance were established in these cases.

The calcium phosphate cements of the first and fourth embodiments according to the present invention each shows a low viscosity in the step of kneading, can be easily kneaded and can be hardened within a relatively short time to give a hardened body having a high strength, even though a kneading liquid is used in a small amount. When brought into contact a pseudo body fluid immediately after the completion of kneading, such a cement is not disintegrated but retains its shape. By further adding polysaccharides such as dextran sulfate to the cement as in the sixth and seventh embodiments according to the present invention, a kneaded body with improved shape impartation can be obtained.

The calcium phosphate cement compositions of the eighth and tenth embodiments according to the present invention each shows a low viscosity in the step of kneading, can be easily kneaded and can be hardened within a relatively short time to give a hardened body having a high strength, even though a kneading liquid is used in a small amount. When brought into contact a pseudo body fluid immediately after the completion of kneading, such a cement is not disintegrated but retains its shape. By further adding polysaccharides such as dextran sulfate to the kneading liquid as in the eleventh and twelfth embodiments according to the present invention, a kneaded body with improved shape impartation can be obtained.

What is claimed is:

1. A calcium phosphate cement comprising a calcium phosphate powder and an N-alkyl-D-glucamine in amount of 0.05 to 5 parts by weight per 100 parts by weight of the calcium phosphate cement, wherein said alkyl is methyl, ethyl, n-propyl or isopropyl.

2. The calcium phosphate cement according to claim 1, wherein said N-alkyl-D-glucamine has an average particle diameter of 0.1 to 100 μm.

3. The calcium phosphate cement according to claim 1, which further comprises dextran in an amount of 1 to 10 parts by weight per 100 parts by weight of the calcium phosphate cement or dextran sulfate in an amount of 5 to 25 parts by weight per 100 parts by weight of the calcium phosphate cement.

4. The calcium phosphate cement according to claim 1, wherein said calcium phosphate powder comprises tetracalcium phosphate and calcium hydrogen phosphate.

5. A calcium phosphate cement comprising a calcium phosphate powder and at least one mono-, di- or triamine selected from the group consisting of methanolamine, ethanolamine, n-propanolamine and isopropanolamine in an amount of 0.05 to 5 parts by weight per 100 parts by weight of the calcium phosphate cement.

6. The calcium phosphate cement according to claim 5, which further comprises dextran in an amount of 1 to 10 parts by weight per 100 parts by weight of the calcium phosphate cement or dextran sulfate in an amount of 5 to 25 parts by weight per 100 parts by weight of the calcium phosphate cement.

7. The calcium phosphate cement according to claim 5, wherein said calcium phosphate powder comprises tetracalcium phosphate and calcium hydrogen phosphate.

8. A calcium phosphate cement composition comprising a calcium phosphate powder and a kneading liquid containing an N-alkyl-D-glucamine in an amount of 0.1 to 10 parts by weight per 100 parts by weight of the kneading liquid, wherein said alkyl is methyl, ethyl, n-propyl or isopropyl and said kneading liquid is contained in an amount of 10 to 25 parts by weight per 100 parts by weight of the calcium phosphate powder.

9. The calcium phosphate cement composition according to claim 8, which further comprises dextran in an amount of 5 to 30 parts by weight per 100 parts by weight of the calcium phosphate cement or dextran sulfate in an amount of 30 to 60 parts by weight per 100 parts by weight of the calcium phosphate cement.

10. The calcium phosphate cement composition according to claim 8, wherein said calcium phosphate powder comprises tetracalcium phosphate and calcium hydrogen.

11. A calcium phosphate cement composition comprising a calcium phosphate powder and a kneading liquid containing at least one mono-, di- or triamine selected from the group consisting of methanolamine, ethanolamine, n-propanolamine and isopropanolamine in an amount of 0.1 to 10 parts by weight per 100 parts by weight of the kneading liquid, and wherein said kneading liquid is contained in an amount of 10 to 25 parts by weight per 100 parts by weight of the calcium phosphate powder.

12. The calcium phosphate cement according to claim 11, which further comprises dextran in an amount of 5 to 30 parts by weight per 100 parts by weight of the calcium phosphate cement or dextran sulfate in an amount of 30 to 60 parts by weight per 100 parts by weight of the calcium phosphate cement.

13. The calcium phosphate cement composition according to claim 11, wherein said calcium phosphate powder comprises tetracalcium phosphate and calcium hydrogen.

* * * * *